United States Patent
Huang et al.

(10) Patent No.: US 12,366,566 B2
(45) Date of Patent: Jul. 22, 2025

(54) PREPARATION METHOD OF PAPER-BASED SENSOR FOR DETECTING AMMONIA GAS, AND USE OF PAPER-BASED SENSOR

(71) Applicant: Jiangsu University, Jiangsu (CN)

(72) Inventors: Xiaowei Huang, Jiangsu (CN); Zhihua Li, Jiangsu (CN); Xiaobo Zou, Jiangsu (CN); Wei Sun, Jiangsu (CN); Jiyong Shi, Jiangsu (CN); Xinai Zhang, Jiangsu (CN); Ning Zhang, Jiangsu (CN); Di Zhang, Jiangsu (CN); Xiaodong Zhai, Jiangsu (CN); Xuetao Hu, Jiangsu (CN); Tingting Shen, Jiangsu (CN)

(73) Assignee: Jiangsu University, Jiangsu (CN)

( * ) Notice: Subject to any disclaimer, the term of this patent is extended or adjusted under 35 U.S.C. 154(b) by 0 days.

(21) Appl. No.: 18/563,925

(22) PCT Filed: May 30, 2023

(86) PCT No.: PCT/CN2023/097121
§ 371 (c)(1),
(2) Date: Nov. 24, 2023

(87) PCT Pub. No.: WO2024/187594
PCT Pub. Date: Sep. 19, 2024

(65) Prior Publication Data
US 2025/0076268 A1   Mar. 6, 2025

(30) Foreign Application Priority Data
Mar. 13, 2023   (CN) .......................... 202310236338.6

(51) Int. Cl.
G01N 33/00   (2006.01)
G01N 21/01   (2006.01)
G01N 21/64   (2006.01)

(52) U.S. Cl.
CPC ......... *G01N 33/0054* (2013.01); *G01N 21/01* (2013.01); *G01N 21/643* (2013.01)

(58) Field of Classification Search
CPC .... G01N 33/0054; G01N 21/01; G01N 21/64; G01N 21/643; Y10T 436/175383; Y10T 436/25; Y10T 436/25125; Y10T 436/25375; Y10T 436/255; Y10T 436/25875
USPC ....... 436/113, 174, 175, 177, 178, 181, 164, 436/166, 167, 169, 172; 422/400, 420, 422/82.05, 82.08, 88, 527, 534
See application file for complete search history.

(56) References Cited

FOREIGN PATENT DOCUMENTS

| CN | 113201325 | 8/2021 |
|---|---|---|
| CN | 114088668 | 2/2022 |
| CN | 114381004 | 4/2022 |
| CN | 115028188 | 9/2022 |
| CN | 115452894 | 12/2022 |
| CN | 115678540 | 2/2023 |

OTHER PUBLICATIONS

Wang et al. Journal of Molecular Structure, vol. 1264, May 8, 2022, pp. 1-6.*
Guo et al. Foods, vol. 11, 2022, pp. 1-12.*
Huang et al. Food Chemistry:X, vol. 21, Dec. 9, 2023, pp. 1-9.*
Prabu Mani et al., ""Turn-on" Fluorescence Sensing and Discriminative Detection of Aliphatic Amines Using a 5-Fold-Interpenetrated Coordination Polymer", Inorganic Chemistry, May 30, 2017, pp. 6772-6775.
Shujun Wang,"Synthesis and Properties of Coordination Polymers Constructed by Polycarboxylates and Multipyridyl Ligands", Thesis of Master Degree, Huaibei Normal University, Sep. 15, 2015, pp. 1-69.
Suna Wang et al., "A Series of Four-Connected Entangled Metal-Organic Frameworks Assembled from Pamoic Acid and Pyridine-Containing Ligands: Interpenetrating, Self-Penetrating, and Supramolecular Isomerism", Crystal Growth & Design, Nov. 7, 2011, pp. 79-92.
"Written Opinion of the International Searching Authority (Form PCT/ISA/237) of PCT/CN2023/097121," mailed on Aug. 24, 2023, pp. 1-4.
"International Search Report (Form PCT/ISA/210) of PCT/CN2023/097121," mailed on Aug. 24, 2023, pp. 1-3.

* cited by examiner

*Primary Examiner* — Maureen Wallenhorst
(74) *Attorney, Agent, or Firm* — JCIPRNET

(57) ABSTRACT

The present disclosure belongs to the technical fields of nanoscience and fluorescence sensing, and specifically relates to a preparation method of a paper-based sensor for detecting an ammonia gas, and a use of the paper-based sensor. In the present disclosure, Zn(PA)(BPE) is first prepared, and a porous structure on a surface of the Zn(PA) (BPE) is used to adsorb an ammonia gas to improve a reaction sensitivity of the ammonia gas; then a Zn(PA) @CNQD ratiometric fluorescent substance is prepared from Zn(PA)(BPE) and CNQD through embedding, and finally dissolved in ultrapure water (UPW) to obtain a solution; and the solution is added dropwise on a filter paper, and the filter paper is purged with nitrogen, such that the solution is loaded on the filter paper to obtain a ratiometric fluorescent paper-based sensor.

10 Claims, 4 Drawing Sheets

PREPARATION METHOD OF PAPER-BASED SENSOR FOR DETECTING AMMONIA GAS, AND USE OF PAPER-BASED SENSOR

CROSS-REFERENCE TO RELATED APPLICATION

This application is a 371 of international application of PCT application serial no. PCT/CN2023/097121, filed on May 30, 2023, which claims the priority benefit of China application no. 202310236338.6, filed on Mar. 13, 2023. The entirety of each of the above mentioned patent applications is hereby incorporated by reference herein and made a part of this specification.

TECHNICAL FIELD

The present disclosure belongs to the technical fields of nanoscience and fluorescence sensing, and specifically relates to a preparation method of a paper-based sensor for detecting an ammonia gas, and a use of the paper-based sensor.

DESCRIPTION OF RELATED ART

An ammonia gas is a gas that has a smaller density than air, a pungent odor, and a toxicity. An ammonia gas is produced due to decarboxylation of amino acids in decaying animal tissues, and is commonly found in chicken and other foods with high-protein meats. Currently, common means for detecting ammonia gases and aliphatic amine gases include gas chromatography-mass spectrometry (GC-MS), electrochemistry, colorimetry, high-performance liquid chromatography (HPLC), and fluorescence detection. However, these methods are often time-consuming and labor-intensive, require complicated pre-treatments, and are not suitable for tests in complicated storage environments. It is simple and convenient to detect ammonia gases and aliphatic amine gases by the fluorescence detection among these detection methods.

Coordination polymers are coordination compounds with different properties that can be obtained by combining different metal ions with different organic ligands, and these coordination compounds each have a stable porous three-dimensional (3D) structure. A porous cavity structure of a coordination polymer has a plurality of reaction sites that can react with a detection object, and has excellent stability. Since the coordination polymers obtained by combining different metal ions with organic ligands have different properties, the coordination polymers have been widely used as materials for detecting ammonia gases and amine gases. Compared with an enhanced fluorescent probe for detecting an ammonia gas, a ratiometric fluorescent probe has the characteristic of dual-wavelength emission, and a change of a wavelength ratio value is independent of a probe concentration and a light source intensity, which can greatly reduce the interference of other detection conditions.

In the prior art, the patent "Sensing Material for Detecting Ammonia Gas, and Preparation Method and Use thereof" (CN 115452894A) is disclosed, which specifically relates to a carbon dot (CD)-based fluorescent probe with low limit of detection (LOD) and high sensitivity. However, the probe has insufficient stability. The patent "Organic Cuprous Halide Material for Efficient Fluorescent Detection of Ammonia Gas, and Preparation and Use thereof" (CN 115028188 A) proposes a fluorescent detection probe with high sensitivity and simple synthesis. However, a material used for the probe is based on the organic cuprous halide material, which exhibits a specified biological toxicity in detection of food spoilage.

At present, most of the materials used for ammonia gas sensing are organic conductive gas-sensitive materials. Such organic conductive gas-sensitive materials have the advantage of high sensitivity, but also have disadvantages such as high cost, poor selectivity, and poor stability. Therefore, it is of great significance to combine a fluorescent probe with a paper base to develop a simple, fast, accurate, portable, and easy-to-operate biosensor.

SUMMARY

In view of the shortcomings of the existing fluorescent molecular probes for detecting an ammonia gas, the present disclosure provides a ratiometric fluorescent probe with high sensitivity and strong stability. In the present disclosure, on the one hand, a porous structure on a surface of Zn(PA) (BPE) adsorbs an ammonia gas to increase a reaction sensitivity to the ammonia gas; and on the other hand, a ratiometric fluorescent probe is prepared from Zn(PA)(BPE) and CNQDs through embedding, which not only makes CNQDs stable, but also improves a background anti-interference ability of detection of the ammonia gas.

In order to achieve the above objective, the present disclosure provides a preparation method of a paper-based sensor for detecting an ammonia gas, including the following steps:

(1) preparation of Zn(PA)(BPE): mixing $Zn(NO_3)_2 \cdot 6H_2O$ with N,N-dimethylformamide (DMF), and stirring a resulting mixture to obtain a solution A; mixing pamoic acid, 1,2-bis(4-pyridyl)ethane, and ultrapure water (UPW) to obtain a mixed solution, and adjusting a pH of the mixed solution with KOH to more than 7.0 to obtain a solution B; mixing the solution A and the solution B, ultrasonically treating a resulting mixed solution, and heating the mixed solution in a high-pressure reactor for a period of time to obtain a solid substance; and washing the solid substance with UPW to obtain a washed solid substance, and vacuum freeze-drying the washed solid substance to obtain a solid powder, which is Zn(PA)(BPE);

(2) preparation of a Zn(PA)@CNQD ratiometric fluorescent substance: mixing specified amounts of sodium citrate, ammonium chloride, and water, adding the Zn(PA)(BPE) powder obtained in the step (1), thoroughly mixing, and transferring a resulting system to a high-pressure reactor; placing the high-pressure reactor in an oven to allow a reaction, and after the reaction is completed, naturally cooling a resulting reaction system to room temperature to obtain a mixture; filling the mixture in a dialysis membrane, and holding the dialysis membrane in a dialysis fluid for a period of time to allow purification, to remove unreacted precursors; and after the purification is completed, collecting a precipitate naturally settled, and freeze-drying the precipitate to obtain a solid powder, which is a Zn(PA)@CNQD ratiometric fluorescent substance; and (3) preparation of a ratiometric fluorescent paper-based sensor by loading a fluorescent probe on a filter paper: dissolving the Zn(PA)@CNQD ratiometric fluorescent substance obtained in the step (2) in UPW to obtain a Zn(PA)@CNQD solution; and adding the Zn(PA) @CNQD solution dropwise on a filter paper, and purging the filter paper with nitrogen, such that the Zn(PA)@CNQD solution is dried and loaded on the filter paper to obtain a ratiometric fluorescent paper-based sensor, which is the paper-based sensor for detecting the ammonia gas.

Preferably, in the step (1), a ratio of the $Zn(NO_3)_2 \cdot 6H_2O$ to the DMF in the solution A is 15 g:200 mL; and the pamoic acid, the 1,2-bis(4-pyridyl)ethane, and the UPW in the solution B are in a ratio of 1.6 g:1.5 g:400 mL.

Preferably, in the step (1), a volume ratio of the solution A to the solution B is 1:5.

Preferably, in the step (1), a concentration of the KOH is 1 M, and the pH is adjusted to 8; and the ultrasonic treatment is conducted for 5 min, and a reaction in the high-pressure reactor is conducted at 120° C. for 72 h.

Preferably, in the step (2), the Zn(PA)(BPE), the sodium citrate, the ammonium chloride, and the water are in a ratio of 20 g:10 g:53 g:500 mL.

Preferably, in the step (2), the reaction in the oven is conducted at 180° C. for 4 h; the dialysis membrane has a molecular weight of 1,000 Da, and the dialysis fluid is selected from a group consisting of UPW, distilled water, and deionized water; and the dialysis membrane is held in the dialysis fluid for 24 h.

In the step (3), preferably, a ratio of the Zn(PA)@CNQD ratiometric fluorescent substance to the UPW is 1.5 mg:(1-128) mL; and more preferably, the ratio of the Zn(PA)@CNQD ratiometric fluorescent substance to the UPW is 1.5 mg:16 mL.

Preferably, in the step (3), the Zn(PA)@CNQD solution is added dropwise on the filter paper in an amount of 15 μL to 20 μL of the Zn(PA)@CNQD solution per $cm^2$ of the filter paper.

A use of the ratiometric fluorescent paper-based sensor prepared by the present disclosure in detection of an ammonia gas is provided, specifically including the following steps:

(1) establishment of a standard curve: placing each of ammonia solutions of different concentrations together with a ratiometric fluorescent paper-based sensor in a same closed environment, where each of the ammonia solutions corresponds to a respective ratiometric fluorescent paper-based sensor; and after a reaction is conducted for a period of time, according to Henry's law, calculating an ammonia gas concentration in a gas phase and calculating a G/B ratio in an RGB value of a corresponding paper-based sensor, and establishing the standard curve correspondingly according to the ammonia gas concentration and the G/B ratio; and (2) detection of a sample: placing a sample solution to be tested and a ratiometric fluorescent paper-based sensor in a same closed environment; and after a reaction is conducted for a period of time, calculating a G/B ratio in an RGB value of the ratiometric fluorescent paper-based sensor, and substituting the G/B ratio into the standard curve obtained in the step (1) to allow detection of an ammonia gas concentration.

Preferably, in the step (1), the ammonia solution has a concentration of 0.1 M to 0.6 M; and in both the step (1) and the step (2), the closed environment has a temperature of 25° C., the reaction is conducted for 24 h, and the ratiometric fluorescent paper-based sensor is arranged adjacent to the ammonia solution or the sample solution to be tested.

Beneficial Effects (1) The Zn(PA)(BPE) prepared by the present disclosure is a porous coordination compound with a stable three-dimensional (3D) structure. Because the coordination compound has high thermal stability, Zn(PA)(BPE) is mixed with a precursor for synthesis of CDs to allow a reaction in the present disclosure, where with structures unchanged, CDs are synthesized in a porous cavity of Zn(PA)(BPE) to obtain a stable composite product Zn(PA)@CNQD, which has two emission wavelengths under excitation of a 365 nm wavelength. Compared with a single-emission fluorescent probe, a ratio of the complex ratiometric fluorescent probe varies independently of a probe concentration and a light source intensity, which can greatly reduce the interference of other detection conditions.

(2) Zn(PA)(BPE) in the complex has a plurality of binding sites, and can react with ammonia to increase the transition of electrons to an energy level orbit, resulting in a fluorescence change. Research results show that LOD of the complex for an ammonia gas can reach 288 nM, and the complex does not react with volatile organic reagents such as acetone, methanol, ethanol, and ethane. Therefore, in the present disclosure, a novel ratiometric fluorescent paper-based sensor with high selectivity and high sensitivity is obtained, which can be packaged and stored together with meat products, and has a promising application prospect in detection of spoilage of meat products.

DESCRIPTION OF THE EMBODIMENTS

Figure 1:
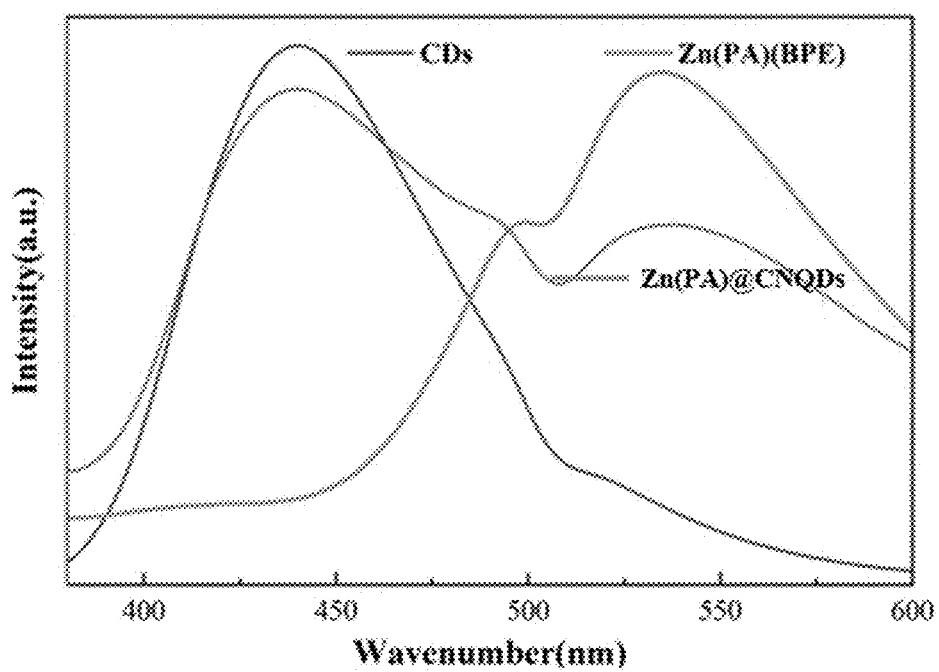
FIG. 1 shows fluorescence emission spectra of Zn(PA)(BPE), CNQD, and Zn(PA)@CNQD ratiometric fluorescent substances.
Figure 2A:
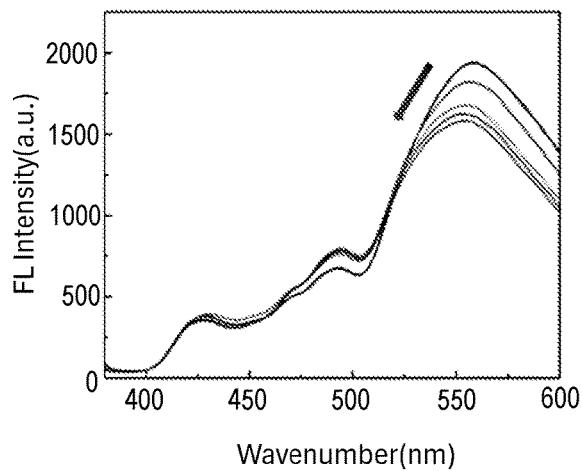
FIG. 2A to FIG. 2H show fluorescence spectra after reactions of Zn(PA)@CNQD solutions of different concentrations with 20 μL of a 0.1 M ammonia solution, where a concentration of the Zn(PA)@CNQD solution in FIG. 2A is 1.5 mg/mL, a concentration of the Zn(PA)@CNQD solution in FIG. 2B is 1.5 mg/2 mL, a concentration of the Zn(PA)@CNQD solution in FIG. 2C is 1.5 mg/4 mL, a concentration of the Zn(PA)@CNQD solution in FIG. 2D is 1.5 mg/8 mL, a concentration of the Zn(PA)@CNQD solution in FIG. 2E is 1.5 mg/16 mL, a concentration of the Zn(PA)@CNQD solution in FIG. 2F is 1.5 mg/32 mL, a concentration of the Zn(PA)@CNQD solution in FIG. 2G is 1.5 mg/64 mL, and a concentration of the Zn(PA)@CNQD solution in FIG. 2H is 1.5 mg/128 mL.
Figure 2B:
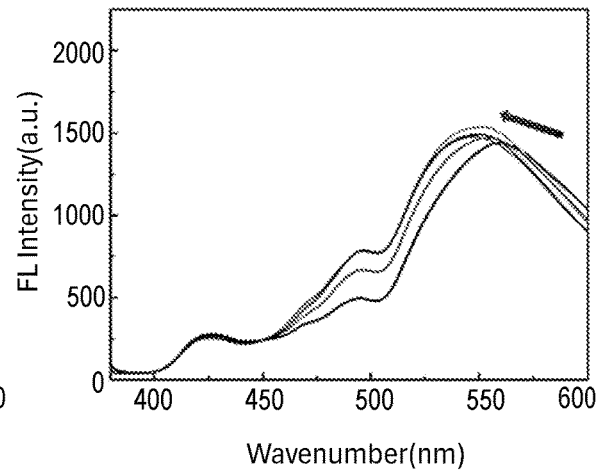
Figure 2C:
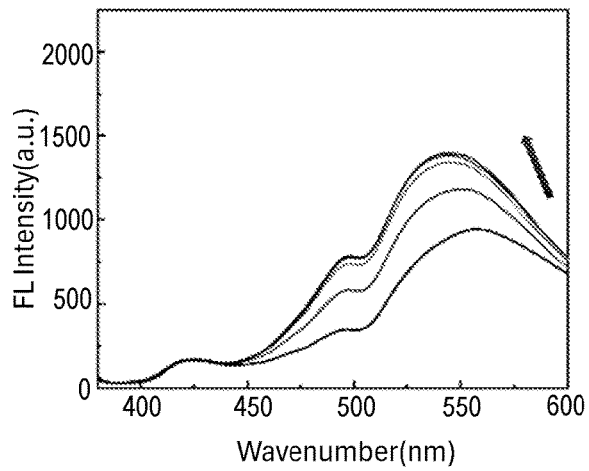
Figure 2D:
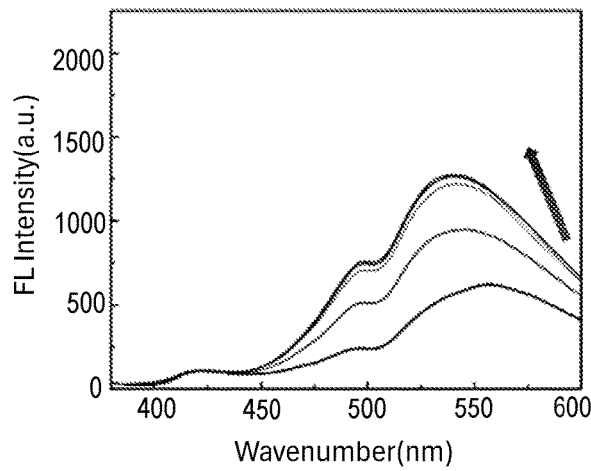
Figure 2E:
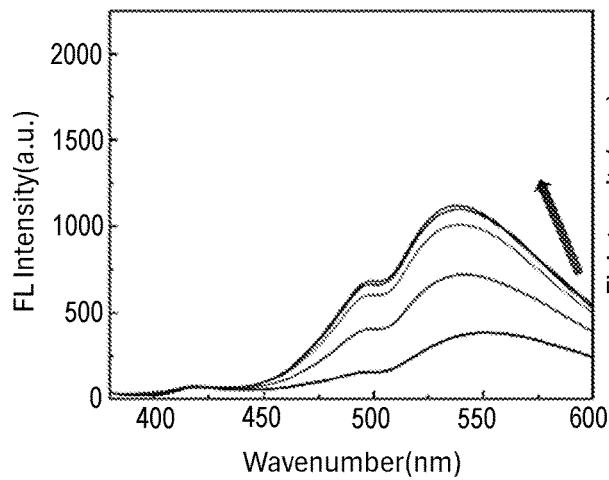
Figure 2F:
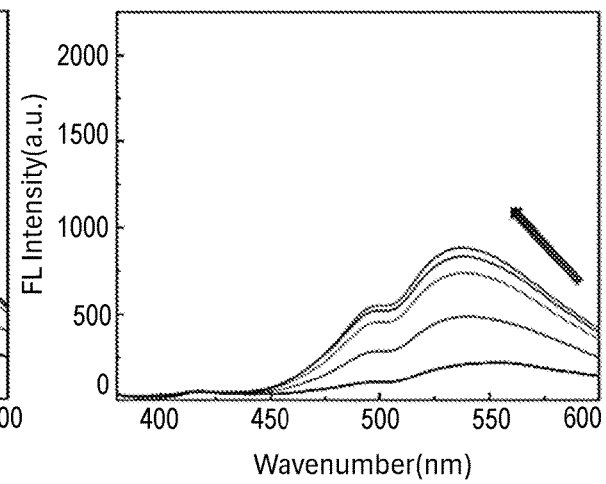
Figure 2G:
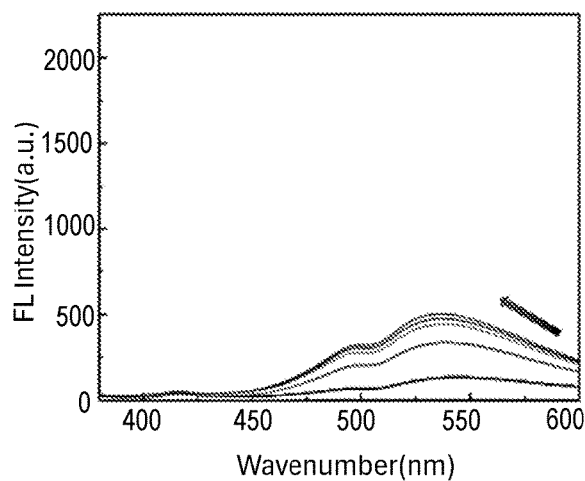
Figure 2H:
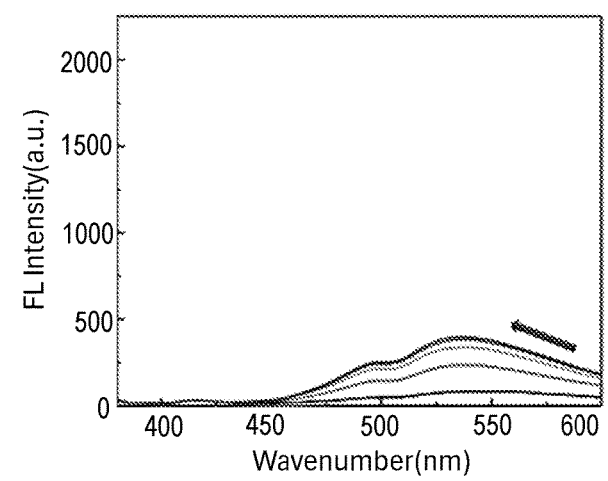

The present disclosure is further described in detail below with reference to the accompanying drawings and specific embodiments.

Example 1

(1) Synthesis of Zn(PA)(BPE):

0.8 mmol of $Zn(NO_3)_2 \cdot 6H_2O$ and 8 mL of DMF were mixed and stirred to obtain a solution A; 0.4 mmol of pamoic acid and 0.8 mmol of 1,2-bis(4-pyridyl)ethane were mixed in 40 mL of UPW to obtain a mixed solution, and a pH of the mixed solution was adjusted with 1 M KOH to 8 to obtain a solution B; the solution A and the solution B were mixed according to a volume ratio of 1:5, and then a resulting mixed solution was ultrasonically treated for 5 min and heated in a high-pressure reactor at 120° C. for 72 h to obtain a solid substance; and the solid substance was washed three times with UPW and then vacuum freeze-dried for 2 d to obtain a solid powder, which was Zn(PA)(BPE).

(2) Preparation of a Zn(PA)@CNQD Ratiometric Fluorescent Substance:

0.1 g of sodium citrate, 0.53 g of ammonium chloride, and 5 mL of water were mixed, then 0.2 g of the Zn(PA)(BPE) powder obtained in step (1) was added, and a resulting mixture was thoroughly mixed and transferred to a high-pressure reactor; the high-pressure reactor was placed in an oven at 180° C. to allow a reaction for 4 h, and a resulting reaction system was naturally cooled to room temperature to obtain a mixture; the mixture was filled in a dialysis membrane with a molecular weight of 1,000 Da, and the dialysis membrane was held in UPW to allow purification for 24 h to remove unreacted precursors to obtain a purified mixture; and the purified mixture was naturally settled, taken out, washed 3 times with UPW, and then vacuum freeze-dried to obtain a product, which was the Zn(PA)@CNQD ratiometric fluorescent substance.

(3) Preparation of a Ratiometric Fluorescent Paper-Based Sensor by Loading a Fluorescent Probe on a Filter Paper:

1.5 mg of the Zn(PA)@CNQD ratiometric fluorescent substance obtained in step (2) was dissolved in 16 mL of pure water to obtain a Zn(PA)@CNQD solution; and 20 μL of the Zn(PA)@CNQD solution was added dropwise on a 1 cm$^2$ filter paper, and the filter paper was purged with nitrogen for 5 min, such that the solution was dried and loaded on the filter paper to obtain a ratiometric fluorescent sensor.

Performance Tests:

1. Test of Optical Properties after the Zn(PA)@CNQD Ratiometric Fluorescent Substance Prepared in Example 1 at Different Concentrations was Reacted with Ammonia (1) Zn(PA)@CNQD aqueous solutions with different concentrations were prepared, and the different concentrations were 1.5 mg/mL, 1.5 mg/2 mL, 1.5 mg/4 mL, 1.5 mg/8 mL, 1.5 mg/16 mL, 1.5 mg/32 mL, 1.5 mg/64 mL, and 1.5 mg/128 mL, respectively.

(2) 200 μL of ammonia water with a concentration of 0.1 M was taken and added to 2 mL of each of the Zn(PA)@CNQD aqueous solutions with different concentrations to obtain mixed solutions, where each Zn(PA)@CNQD aqueous solution corresponded to one part of ammonia water; and the mixed solutions each were allowed to stand for 5 min, and then a fluorescence intensity of each of the mixed solutions was detected. It can be seen from FIG. 2A to FIG. 2H that the reactions of the complexes of different concentrations with ammonia water of a same concentration lead to different fluorescence enhancement sizes. Therefore, it can be inferred that, when a concentration of Zn(PA)@CNQD is too high, the autofluorescence is quenched due to an inner filter effect of fluorescence after Zn(PA)@CNQD reacts with ammonia water. In order to make a Zn(PA)@CNQD ratiometric fluorescent substance well react with an ammonia gas, Zn(PA)@CNQD with a concentration of 1.5 mg/16 mL is selected in the present disclosure.

2. Method for Detecting an Ammonia Gas with the Zn(PA)@CNQD Paper-Based Sensor Prepared in Example 1

(1) The ratiometric fluorescent sensor prepared in Example 1 was used to detect an ammonia gas concentration, and a concentration of the paper-based sensor was calculated through the following formula:

$$C(\text{sensors}) = \frac{c(Zn(PA)@CNQDs) \cdot v(Zn(PA)@CNQDs)}{A(\text{paper})}$$

where c(Zn(PA)@CNQDs) represents a concentration of a Zn(PA)@CNQD solution; v(Zn(PA)@CNQDs) represents a volume of a Zn(PA)@CNQD solution; and A(paper) represents an area of a filter paper.

(2) Ammonia solutions with different concentrations each were placed in a same closed environment as the ratiometric fluorescent paper-based sensor. In this example, a gas generator was selected as the closed environment. The dry ratiometric fluorescent sensor was fixed in the gas generator, a same volume of each of the ammonia solutions with different concentrations (0 M, 0.1 M, 0.2 M, 0.3 M, 0.4 M, 0.5 M, and 0.6 M) was added to a well of the gas generator, and then the gas generator was sealed, such that the ratiometric fluorescent sensor and the ammonia solution were in a same closed environment; and the gas generator was placed in a 25° C. environment, and a concentration in an ammonia gas phase of the gas generator was calculated through the following formula:

$$P = \frac{n(NH_3, g) \cdot R \cdot T}{V(NH_3, g)} = K_B \cdot \frac{n_0(NH_3 \cdot H_2O) - n(NH_3, g)}{n_0(NH_3 \cdot H_2O) - n(NH_3, g) + \frac{v(H_2O) \cdot \rho(H_2O)}{M(H_2O)}}$$

where R represents a molar gas constant; T represents a reaction ambient temperature; n(NH$_3$, g) represents a molar amount of an ammonia gas in a gas phase; V(NH$_3$, g) represents a volume of a container; K$_B$ represents a Henry's constant; n$_0$(NH$_3$·H$_2$O) represents a molar amount of ammonia water; V(H$_2$O) represents a total volume of a solution; ρ(H$_2$O) represents a density of water; and M(H$_2$O) represents a relative molecular mass of water.

(3) After the reaction was conducted for 24 h, a fluorescence color of the ratiometric fluorescent sensor under an ultraviolet (UV) lamp of 365 nm was recorded by a smart phone, and once a paper-based fluorescence image change at each concentration was recorded, a paper base was changed to observe the next concentration (that is, one Zn(PA)@CNQD paper-based sensor corresponded to one concentration). The above operation was repeated three times at each concentration. A fluorescence color of the paper-based sensor gradually changed from blue-green to bright-green, and the higher the ammonia gas concentration, the brighter the green fluorescence of a corresponding sensor.

Figure 3:
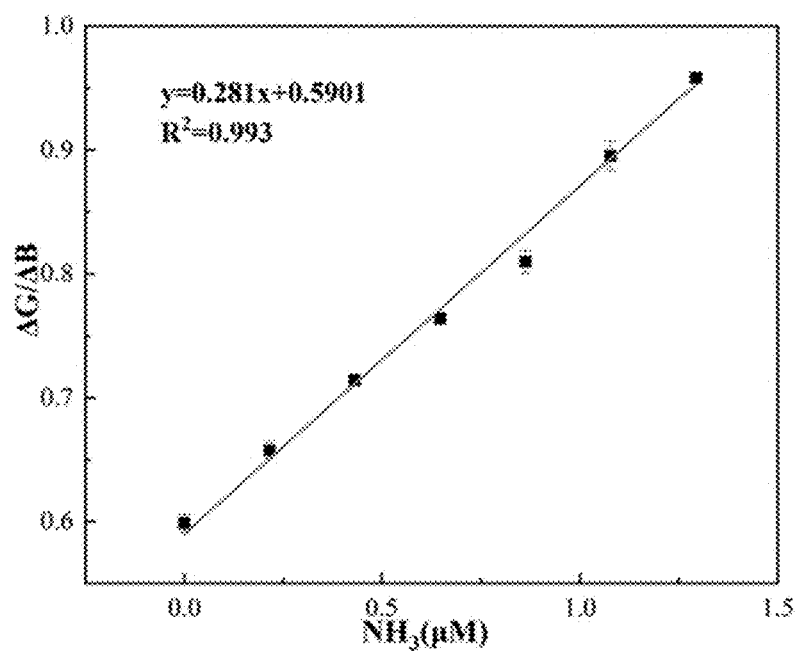
FIG. 3 shows a standard curve established based on a relationship between G/B of a fluorescence image of a paper-based sensor and an ammonia gas concentration.

An RGB value of an image was extracted to calculate a ratio of a G value to a B value, thereby allowing the quantification analysis of an ammonia gas. According to a relationship between G/B and an ammonia gas concentration, a standard curve was established (FIG. 3), where an equation of the standard curve was y=0.281 x+0.5901 (R$^2$=0.993), and LOD was 288 nM. It can be seen from the results that the standard curve has an excellent linear relationship, and the LOD is low, indicating an excellent ammonia gas detection effect.

Figure 4:
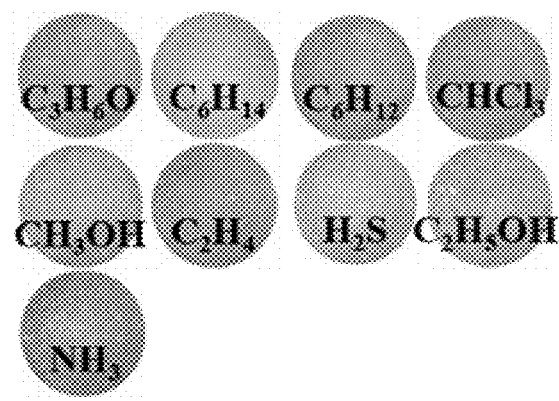
FIG. 4 shows fluorescence color changes after reactions of a paper-based sensor with different organic volatile gases.

(4) The ratiometric fluorescent sensor and a volatile organic solution with a same concentration (0.1 M)

were placed in a same environment, a resulting system was allowed to stand for a period of time, and a fluorescence color of the ratiometric fluorescent sensor under a UV lamp of 365 nm was recorded by a smart phone. Except that the ratiometric fluorescent sensor became bright-green at an ammonia gas concentration of 0.1 M, a fluorescence color of the ratiometric fluorescent sensor almost remained unchanged and was still blue-green under other volatile gases. Results were shown in FIG. 4. It can be seen that the sensor has excellent selectivity for an ammonia gas.

Figure 5:
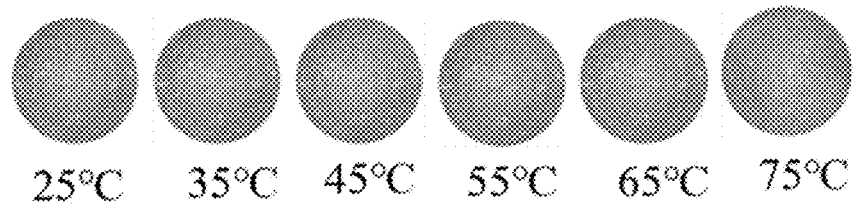
FIG. 5 shows fluorescence color changes after reactions of a paper-based sensor for 1 h at different temperatures.

(5) The paper-based sensor was held for 1 h at different temperatures (25° C., 35° C., 45° C., 55° C., 65° C., and 75° C.), a fluorescence color of the paper-based sensor under a UV lamp of 365 nm was recorded by a smart phone, and an RGB value in an image was extracted. Results were shown in Table 1. It can be seen from FIG. 5 that G and B values of the sensor do not change significantly in a temperature range from 25° C. to 65° C., while the G value does not change significantly and the B value decreases slightly at 75° C. It can be seen that the ratiometric fluorescent sensor has excellent stability.

TABLE 1

G and B values extracted after the paper-based sensor is held for 1 h at different temperatures

| Temperature/° C. | 25 | 35 | 45 | 55 | 65 | 75 |
|---|---|---|---|---|---|---|
| G | 141 | 145 | 139 | 144 | 140 | 121 |
| B | 235 | 240 | 230 | 233 | 235 | 225 |

(6) Through the standard curve, a G/B value of a fluorescence color of the paper-based sensor could be acquired to obtain a corresponding ammonia gas concentration.

Ammonia water samples with concentrations of 0.25 M, 0.45 M, and 0.55 M respectively were prepared, and 1 mL of each of the three samples was taken and placed in the same environment (25° C.) as the paper-based sensor to allow a reaction. According to the formula in step (2), corresponding ammonia gas concentrations were calculated to be 0.53899 µM, 0.97017 µM, and 1.18576 µM, respectively. After the reaction was conducted for 24 h, an RGB value of a corresponding paper-based sensor was acquired, and a G/B value was calculated and substituted into the standard curve in step (3) to obtain a corresponding ammonia gas concentration, which was compared with an actual ammonia gas concentration. Results were shown in Table 2.

TABLE 2

Measurement results of ammonia gas samples and recovery rates

| Sample | Spiked amount (µM) | Measured amount (µM) | Recovery rate (%) |
|---|---|---|---|
| 1 | 0.53899 | 0.46892 | 87 |
| 2 | 0.97017 | 1.04778 | 108 |
| 3 | 1.18576 | 1.06718 | 90 |

It can be seen from Table 2 that the recovery rates are 87%, 108%, and 90%, respectively. The recovery rates are excellent and the results are relatively accurate, indicating that a corresponding ammonia gas concentration can be obtained through an RGB change value of a fluorescence color of the paper-based sensor within a specified ammonia gas concentration range.

The above examples are merely intended to illustrate the present disclosure, rather than to limit the technical solutions described in the present disclosure. Therefore, although the present disclosure is described in detail in this specification with reference to the above examples, those of ordinary skill in the art should understand that the present disclosure can still be modified or equivalently replaced. All technical solutions and improvements thereof made without deviating from the spirit and scope of the present disclosure should be covered by the scope of the claims of the present disclosure.

What is claimed is:

1. A preparation method of a paper-based sensor for detecting an ammonia gas, comprising the following steps:
   step (1) mixing $Zn(NO_3)_2 \cdot 6H_2O$ with N,N-dimethylformamide (DMF), and stirring a resulting mixture to obtain a solution A; mixing pamoic acid, 1,2-bis(4-pyridyl) ethane, and ultrapure water to obtain a mixed solution, and adjusting a pH of the mixed solution with KOH to more than 7.0 to obtain a solution B; mixing the solution A and the solution B, ultrasonically treating a resulting mixed solution, and heating the mixed solution in a high-pressure reactor for a period of time to obtain a solid substance; and washing the solid substance with ultrapure water to obtain a washed solid substance, and vacuum freeze-drying the washed solid substance to obtain a solid powder, which is zinc (pamoic acid)(1,2-bis(4-pyridyl) ethane) (Zn(PA)(BPE));
   step (2) mixing specified amounts of sodium citrate, ammonium chloride, and water, adding the Zn(PA)(BPE) obtained in the step (1), thoroughly mixing, and transferring a resulting system to a high-pressure reactor; placing the high-pressure reactor in an oven to allow a reaction, and after the reaction is completed, naturally cooling a resulting reaction system to room temperature to obtain a mixture; filling the mixture in a dialysis membrane, and holding the dialysis membrane in a dialysis fluid for a period of time to allow purification, to remove unreacted precursors; and after the purification is completed, collecting a precipitate naturally settled, and freeze-drying the precipitate to obtain a solid powder, which is a zinc(pamoic acid)@carbon nanotube quantum dots (Zn(PA)@CNQD) ratiometric fluorescent substance; and
   step (3) dissolving the Zn(PA)@CNQD ratiometric fluorescent substance obtained in the step (2) in ultrapure water to obtain a Zn(PA)@CNQD solution; and adding the Zn(PA)@CNQD solution dropwise on a filter paper, and purging the filter paper with nitrogen, such that the Zn(PA)@CNQD solution is dried and loaded on the filter paper to obtain a ratiometric fluorescent paper-based sensor, which is the paper-based sensor for detecting the ammonia gas.

2. The preparation method of the paper-based sensor for detecting the ammonia gas according to claim 1, wherein in the step (1), a ratio of the $Zn(NO_3)_2 \cdot 6H_2O$ to the DMF in the solution A is 15 g:200 mL; the pamoic acid, the 1,2-bis(4-pyridyl) ethane, and the ultrapure water in the solution B are in a ratio of 1.6 g:1.5 g:400 mL; and a volume ratio of the solution A to the solution B is 1:5.

3. The preparation method of the paper-based sensor for detecting the ammonia gas according to claim 1, wherein in the step (1), a concentration of the KOH is 1 M, and the pH is adjusted to 8; and the ultrasonic treatment is conducted for 5 min, and a reaction in the high-pressure reactor is conducted at 120° C. for 72 h.

4. The preparation method of the paper-based sensor for detecting the ammonia gas according to claim 1, wherein in the step (2), the Zn(PA)(BPE), the sodium citrate, the ammonium chloride, and the water are in a ratio of 20 g:10 g:53 g:500 mL.

5. The preparation method of the paper-based sensor for detecting the ammonia gas according to claim 1, wherein in the step (2), the reaction in the oven is conducted at 180° C. for 4 h; the dialysis membrane has a molecular weight of 1,000 Da, and the dialysis fluid is selected from a group consisting of ultrapure water, distilled water, and deionized water; and the dialysis membrane is held in the dialysis fluid for 24 h.

6. The preparation method of the paper-based sensor for detecting the ammonia gas according to claim 1, wherein in the step (3), a ratio of the Zn(PA)@CNQD ratiometric fluorescent substance to the ultrapure water is 1.5 mg: (1-128) mL.

7. The preparation method of the paper-based sensor for detecting the ammonia gas according to claim 6, wherein the ratio of the Zn(PA)@CNQD ratiometric fluorescent substance to the ultrapure water is 1.5 mg: 16 mL.

8. The preparation method of the paper-based sensor for detecting the ammonia gas according to claim 1, wherein in the step (3), the Zn(PA)@CNQD solution is added dropwise on the filter paper in an amount of 15 μL to 20 μL of the Zn(PA)@CNQD solution per $cm^2$ of the filter paper.

9. A method for detecting an ammonia gas using the ratiometric paper-based sensor prepared by the method according to claim 1, comprising the following steps:

step (1) establishment of a standard curve: placing each of ammonia solutions of different concentrations together with the ratiometric fluorescent paper-based sensor in a same closed environment, wherein each of the ammonia solutions corresponds to a respective ratiometric fluorescent paper-based sensor; and after a reaction is conducted for a period of time, according to Henry's law, calculating an ammonia gas concentration in a gas phase and calculating a green/blue (G/B) ratio in a red-green-blue (RGB) value of a corresponding paper-based sensor, and establishing the standard curve correspondingly according to the ammonia gas concentration and the G/B ratio; and step (2) detection of a sample: placing a sample solution to be tested and the ratiometric fluorescent paper-based sensor in the same closed environment; and after a reaction is conducted for a period of time, calculating a G/B ratio in an RGB value of the ratiometric fluorescent paper-based sensor, and substituting the G/B ratio into the standard curve obtained in the step (1) to allow detection of an ammonia gas concentration.

10. The method according to claim 9, wherein in the step (1), the ammonia solutions have a concentration of 0.1 M to 0.6 M; and in both the step (1) and the step (2), the same closed environment has a temperature of 25° C., the reaction is conducted for 24 h, and each of the ratiometric fluorescent paper-based sensors are arranged adjacent to the ammonia solutions of different concentrations or the sample solution to be tested.

* * * * *